United States Patent [19]
Foley et al.

[11] Patent Number: 6,007,487
[45] Date of Patent: Dec. 28, 1999

[54] TISSUE RETRACTOR FOR USE THROUGH A CANNULA

[75] Inventors: Kevin Thomas Foley, Germantown; Maurice Mell Smith, Cordova; John B. Clayton, Germantown; Joseph Moctezuma, Memphis, all of Tenn.

[73] Assignee: SDGI Holdings, Inc., Wilmington, Del.

[21] Appl. No.: 08/920,991

[22] Filed: Aug. 29, 1997

Related U.S. Application Data

[62] Division of application No. 08/620,933, Mar. 22, 1996, Pat. No. 5,792,044.

[51] Int. Cl.$^6$ ..................................................... A61B 1/313
[52] U.S. Cl. .......................... 600/235; 600/210; 600/204
[58] Field of Search ..................................... 600/201, 204, 600/206, 210, 235

[56] References Cited

U.S. PATENT DOCUMENTS

| | | |
|---|---|---|
| 465,161 | 12/1891 | Chase . |
| 2,235,979 | 3/1941 | Brown . |
| 2,255,657 | 9/1941 | Freedman . |
| 2,482,116 | 9/1949 | Lanahan . |
| 2,575,253 | 11/1951 | Bicek ...................................... 600/210 |
| 2,666,428 | 1/1954 | Glenner ................................... 600/210 |
| 2,756,742 | 7/1956 | Barton . |
| 2,829,649 | 4/1958 | Glenner ............................... 600/210 X |
| 2,886,004 | 5/1959 | Morrison . |
| 3,486,505 | 12/1969 | Morrison . |
| 3,570,498 | 3/1971 | Weighton . |
| 3,626,471 | 12/1971 | Florin . |
| 3,651,800 | 3/1972 | Wilbanks ................................ 600/210 |
| 3,941,127 | 3/1976 | Froning . |
| 3,964,480 | 6/1976 | Froning . |
| 4,049,000 | 9/1977 | Williams . |

(List continued on next page.)

FOREIGN PATENT DOCUMENTS

| | | |
|---|---|---|
| 1 566 116 | 1/1970 | European Pat. Off. . |
| 0 303 824 | 2/1989 | European Pat. Off. . |
| 0 528 562 A2 | 2/1993 | European Pat. Off. . |

(List continued on next page.)

OTHER PUBLICATIONS

*Laparoscopic Bone Dowel Surgical Technique* Sofamor Danek The Spine Specialist.
*Spinal Endoscopy, Evolution, Applications & Foundations*; Hallett H. Mathews, M.D.
*Laparoscopic Bone Dowel Instruments Brochure*; Sofamor Danek, 1995.
*Micro–Endo Systems Brochure*; Sofamor Danek, 1994.

*Primary Examiner*—John P. Leubecker
*Attorney, Agent, or Firm*—Woodard, Emhardt, Naughton, Moriarty & McNett Patent and Trademark Attorneys

[57] ABSTRACT

Devices and methods for performing percutaneous spinal surgery under direct visualization and through a single cannula are shown. A device (10) is provided which includes an elongated cannula (20) having a first inner diameter ($D_I$) and an outer diameter ($D_O$) sized for percutaneous introduction into a patient. The cannula (20) defines a working channel (25) between its ends (21, 22) which has a second diameter ($D_2$) equal to the diameter ($D_I$) of the cannula sized for receiving a tool therethrough. An elongated viewing element (50) is engageable to the cannula (20) adjacent the working channel (25), preferably by a fixture (30). The fixture (30) includes a housing (31) attachable to the proximal end (22) of the cannula (20) that defines a working channel opening (35) which is in communication with the working channel (25). The housing (31) also defines an optics bore (60) adjacent the working channel opening (35). In certain embodiments, the fixture (30) supports the viewing element (50) for translation and/or rotation within the optics bore (60) along the longitudinal axis of the bore, and for rotation of the housing (31) relative to the cannula (20) so that the longitudinal axis of the optics bore (60) will rotate about the longitudinal axis of the working channel (25). Methods are also provided for performing spinal surgeries percutaneously with direct visualization and without the requirement for a fluid-maintained workspace.

22 Claims, 7 Drawing Sheets

U.S. PATENT DOCUMENTS

| | | |
|---|---|---|
| 4,232,660 | 11/1980 | Coles ........................................ 600/210 |
| 4,344,419 | 8/1982 | Burgin . |
| 4,350,151 | 9/1982 | Scott . |
| 4,461,281 | 7/1984 | Carson . |
| 4,498,902 | 2/1985 | Ash et al. . |
| 4,545,374 | 10/1985 | Jacobson . |
| 4,562,832 | 1/1986 | Wilder et al. . |
| 4,573,448 | 3/1986 | Kambin . |
| 4,586,491 | 5/1986 | Carpenter . |
| 4,638,799 | 1/1987 | Moore . |
| 4,655,216 | 4/1987 | Tischer . |
| 4,674,501 | 6/1987 | Greenberg . |
| 4,678,459 | 7/1987 | Onik et al. . |
| 4,700,694 | 10/1987 | Shishido . |
| 4,736,738 | 4/1988 | Lipovsek et al. . |
| 4,750,475 | 6/1988 | Yoshihashi . |
| 4,750,487 | 6/1988 | Zanetti . |
| 4,762,120 | 8/1988 | Hussein . |
| 4,875,897 | 10/1989 | Lee . |
| 4,899,729 | 2/1990 | Gill et al. . |
| 4,905,082 | 2/1990 | Nishigaki et al. . |
| 4,947,896 | 8/1990 | Bartlett . |
| 4,972,827 | 11/1990 | Kishi et al. . |
| 5,004,457 | 4/1991 | Wyatt et al. . |
| 5,071,410 | 12/1991 | Pazell . |
| 5,125,396 | 6/1992 | Ray . |
| 5,158,543 | 10/1992 | Lazarus . |
| 5,171,279 | 12/1992 | Mathews . |
| 5,195,541 | 3/1993 | Obenchain . |
| 5,201,729 | 4/1993 | Hertzmann et al. . |
| 5,242,444 | 9/1993 | MacMillan . |
| 5,334,150 | 8/1994 | Kaali . |
| 5,354,302 | 10/1994 | Ko . |
| 5,357,983 | 10/1994 | Mathews . |
| 5,376,076 | 12/1994 | Kaali . |
| 5,380,291 | 1/1995 | Kaali . |
| 5,392,766 | 2/1995 | Masterson et al. . |
| 5,395,317 | 3/1995 | Kambin . |
| 5,396,880 | 3/1995 | Kagan et al. . |
| 5,437,637 | 8/1995 | Lieber et al. . |
| 5,439,449 | 8/1995 | Mapes et al. . |
| 5,439,464 | 8/1995 | Shapiro . |
| 5,441,041 | 8/1995 | Sauer et al. . |
| 5,443,058 | 8/1995 | Ough . |
| 5,445,142 | 8/1995 | Hassler, Jr. . |
| 5,472,426 | 12/1995 | Bonati et al. . |
| 5,534,009 | 7/1996 | Lander . |
| 5,551,947 | 9/1996 | Kaali . |
| 5,562,696 | 10/1996 | Nobles et al. . |
| 5,603,688 | 2/1997 | Upsher . |
| 5,667,472 | 9/1997 | Finn et al. . |
| 5,667,473 | 9/1997 | Finn et al. . |
| 5,667,478 | 9/1997 | McFarlin et al. . |

FOREIGN PATENT DOCUMENTS

| | | |
|---|---|---|
| 2 714 285 | 6/1995 | European Pat. Off. . |
| 2 701 379 A1 | 8/1994 | France . |
| 3936811 A1 | 9/1990 | Germany . |
| 2 234 906 | 2/1991 | United Kingdom . |
| WO 92/19146 | 11/1992 | WIPO . |
| WO 93/14801 | 8/1993 | WIPO . |
| WO 93/15647 | 8/1993 | WIPO . |
| WO 95/2285 | 8/1995 | WIPO . |

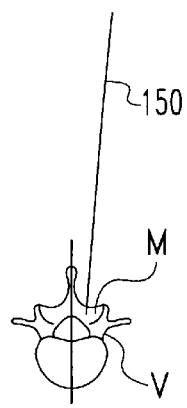
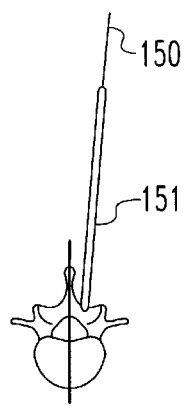
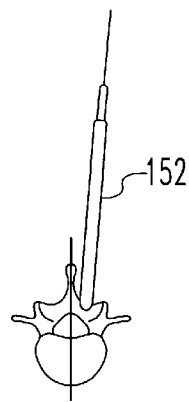
Fig. 10a    Fig. 10b    Fig. 10c
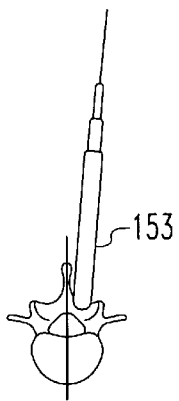
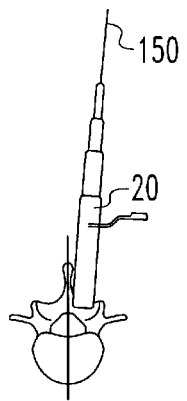
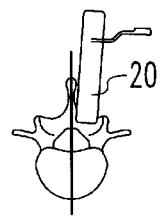
Fig. 10d    Fig. 10e    Fig. 10f
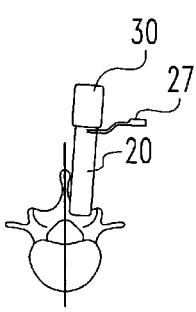
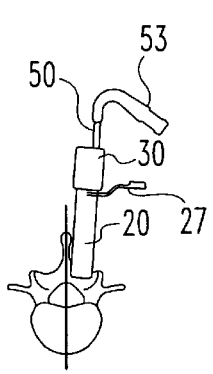
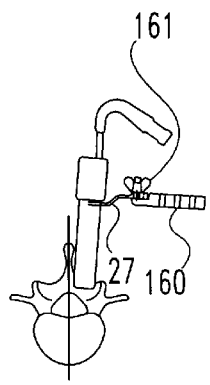
Fig. 10g    Fig. 10h    Fig. 10i

TISSUE RETRACTOR FOR USE THROUGH A CANNULA

This application is a division of application Ser. No. 08/620,933, filed Mar. 22, 1996, now U.S. Pat. No. 5,792,044.

FIELD OF THE INVENTION

The present invention relates to devices, instruments and methods for performing percutaneous surgeries, particularly at locations deep within the body. One specific application of the invention concern devices, instruments and techniques for percutaneous, minimally invasive spinal surgery. In another aspect of the invention, the percutaneous surgery is performed under direct vision at any location in the body.

BACKGROUND OF THE INVENTION

Traditional surgical procedures for pathologies located deep within the body can cause significant trauma to the intervening tissues. These open procedures often require a long incision, extensive muscle stripping, prolonged retraction of tissues, denervation and devascularization of tissue. Most of these surgeries require a recovery room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention.

Minimally invasive alternatives such as arthroscopic techniques reduce pain, post-operative recovery time and the destruction of healthy tissue. Orthopedic surgical patients have particularly benefitted from minimally invasive surgical techniques. The site of pathology is accessed through portals rather than through a significant incision thus preserving the integrity of the intervening tissues. These minimally invasive techniques also often require only local anesthesia. The avoidance of general anesthesia reduces post-operative recovery time and the risk of complications.

Minimally invasive surgical techniques are particularly desirable for spinal and neurosurgical applications because of the need for access to locations deep within the body and the danger of damage to vital intervening tissues. For example, a common open procedure for disc herniation, laminectomy followed by discectomy requires stripping or dissection of the major muscles of the back to expose the spine. In a posterior approach, tissue including spinal nerves and blood vessels around the dural sac, ligaments and muscle must be retracted to clear a channel from the skin to the disc. These procedures normally take at least one-two hours to perform under general anesthesia and require post-operative recovery periods of at least several weeks. In addition to the long recovery time, the destruction of tissue is a major disadvantage of open spinal procedures. This aspect of open procedures is even more invasive when the discectomy is accompanied by fusion of the adjacent vertebrae. Many patients are reluctant to seek surgery as a solution to pain caused by herniated discs and other spinal conditions because of the severe pain sometimes associated with the muscle dissection.

In order to reduce the post-operative recovery time and pain associated with spinal and other procedures, micro-surgical techniques have been developed. For example, in micro-surgical discectomies, the disc is accessed by cutting a channel from the surface of the patient's back to the disc through a small incision. An operating microscope or loupes is used to visualize the surgical field. Small diameter micro-surgical instruments are passed through the small incision and between two laminae and into the disc. The intervening tissues are disrupted less because the incision is smaller. Although these micro-surgical procedures are less invasive, they still involve some of the same complications associated with open procedures, such as injury to the nerve root and dural sac, perineural scar formation, reherniation at the surgical site and instability due to excess bone removal.

Other attempts have been made for minimally invasive procedures to correct symptomatic spinal conditions. One example is chemonucleolysis which involved the injection of an enzyme into the disc to partially dissolve the nucleus to alleviate disc herniation. Unfortunately, the enzyme, chymopapain, has been plagued by concerns about both its effectiveness and complications such as severe spasms, post-operative pain and sensitivity reactions including anaphylactic shock.

The development of percutaneous spinal procedures has yielded a major improvement in reducing recovery time and post-operative pain because they require minimal, if any, muscle dissection and they can be performed under local anesthesia. For example, U.S. Pat. No. 4,545,374 to Jacobson discloses a percutaneous lumbar discectomy using a lateral approach, preferably under fluoroscopic X-ray. This procedure is limited because it does not provide direct visualization of the discectomy site.

Other procedures have been developed which include arthroscopic visualization of the spine and intervening structures. U.S. Pat. Nos. 4,573,448 and 5,395,317 to Kambin disclose percutaneous decompression of herniated discs with a posterolateral approach. Fragments of the herniated disc are evacuated through a cannula positioned against the annulus. The '317 Kambin patent discloses a biportal procedure which involves percutaneously placing both a working cannula and a visualization cannula for an endoscope. This procedure allows simultaneous visualization and suction, irrigation and resection in disc procedures.

Unfortunately, disadvantages remain with these procedures and the accompanying tools because they are limited to a specific application or approach. For example, Jacobson, Kambin and other references require a lateral or a posterolateral approach for percutaneous discectomy. These approaches seek to avoid damage to soft tissue structures and the need for bone removal because it was thought to be impractical to cut and remove bone through a channel. However, these approaches do not address other spinal conditions which may require a mid-line approach, removal of bone or implants.

U.S. Pat. No. 5,439,464 to Shapiro discloses a method and instruments for performing arthroscopic spinal surgeries such as laminectomies and fusions with a mid-line or medial posterior approach using three cannulas. Each of the cannulas requires a separate incision. While Shapiro discloses an improvement over prior procedures which were limited to a posterolateral or lateral approach for disc work, Shapiro's procedure still suffers from many of the disadvantages of known prior percutaneous spinal surgery techniques and tools. One disadvantage of the Shapiro procedure is its requirement of a fluid working space. Another significant detriment is that the procedure requires multiple portals into the patient.

Fluid is required in these prior procedures to maintain the working space for proper function of optics fixed within a prior art cannula and inserted percutaneously. Irrigation, or the introduction of fluid into the working space, can often be logistically disadvantageous and even dangerous to the patient for several reasons. The introduction of fluid into the working space makes hemostasis more difficult and may damage surrounding tissue. Excess fluid may dangerously dilute the sodium concentration of the patient's blood supply which can cause seizures or worse. The fluid environment can also make drilling difficult due to cavitation. The requirement for a fluid environment generally increases expenses associated with the surgery and adds to the complexity of the surgery, due in part to the relatively high volume of fluid required.

A need has remained for devices and methods that provide for percutaneous minimally invasive surgery for all applications and approaches. A need has also remained for percutaneous methods and devices which do not require a fluid-filled working space, but that can be adapted to a fluid environment is necessary.

A significant need if present in this field for techniques and instruments that permit surgical procedures in the working space under direct vision. Procedures that reduce the number of entries into the patient are also highly desirable. The fields of spinal and neuro surgery have particularly sought devices and techniques that minimize the invasion into the patient and that are streamlined and concise in their application.

SUMMARY OF THE INVENTION

Briefly describing one aspect of the invention, there is provided devices and method for performing percutaneous procedures under direct visualization, even at locations deep within a patient. In one embodiment, a device for use in percutaneous surgery includes an elongated cannula having a first inner diameter and an outer diameter sized for percutaneous introduction into a patient. The cannula further includes a distal working end and an opposite proximal end and defines a working channel between the ends having a second diameter which is equal to the first inner diameter. The working channel is sized to receive a tool therethrough. The device also includes an elongated viewing element mounted inside the cannula adjacent the working channel. The viewing element has a first end connectable to a viewing apparatus and an opposite second end disposed adjacent the distal working end of the cannula.

In another aspect, a fixture is provided for mounting the elongated viewing element to the cannula. The fixture includes a housing attachable to the proximal end of the cannula. The housing defines a working channel opening therethrough in communication with the working channel. The working channel opening is sized to substantially correspond to the second diameter of the working channel. The housing also defines an optics bore adjacent the working channel opening. The optics bore is sized to receive the elongated viewing element therethrough.

In some embodiments, the fixture supports the viewing device for movement within the optics bore along the longitudinal axis of the bore to extend or retract the lens relative to the distal working end of the cannula. In other embodiments, the fixture supports the viewing device for rotation within the optics bore about the longitudinal axis of the bore. In some embodiments, the housing is rotatable relative to the cannula so that the longitudinal axis of the optics bore is rotatable about the longitudinal axis of the working channel.

Novel tools are also provided which are insertable into the working channel of the cannula. A tissue retractor in one embodiment includes a body and an integral working tip configured to atraumatically displace tissue as the retractor is manipulated through tissue. The body has a convex surface configured to conform to the inner cylindrical surface of the cannula and an opposite concave surface which does not obstruct the working channel or visualization of the working space. Cannulated tissue dilators are also provided which are insertable over a guidewire or another dilator as well as insertable into the working channel. In some embodiments, the tissue dilators include a tapered working end to displace tissue and a gripping portion having a number of circumferential grooves to enhance gripping and manipulation of the dilator.

According to the methods of this invention, spinal and other surgeries can be performed percutaneously with direct visualization without the requirement for a fluid-maintained working space. In another aspect of the inventive surgical techniques, all steps of a surgical procedure are conducted under direct vision through a single working channel cannula. An optical scope or viewing device is moved within the working channel and throughout the working space from a variety of angles and orientations to provide a clear view of the operative steps.

The techniques of the present invention also encompass passing multiple tools and instruments through the single working channel cannula and manipulating the instruments and tools within the working space. In one specific embodiment, a tissue retractor is provided that extends through the working channel without significantly reducing the dimensions of the channel.

It is an object of the invention to provide devices and methods for percutaneous spinal surgery for all applications and approaches. One advantage of this invention is that percutaneous procedures can be accomplished in a dry environment because a fluid working space is not required for the proper function of the optics. One benefit of this invention is that it provides instruments and methods which reduce the cost, risk, pain and recovery time associated with surgery. These and other objects, advantages and features are accomplished according to the devices and methods of the present invention.

DESCRIPTION OF THE FIGURES

FIG. 10 (a)–(i) depicts the steps of a method according to this invention.

DESCRIPTION OF THE PREFERRED EMBODIMENTS

Figure 1:
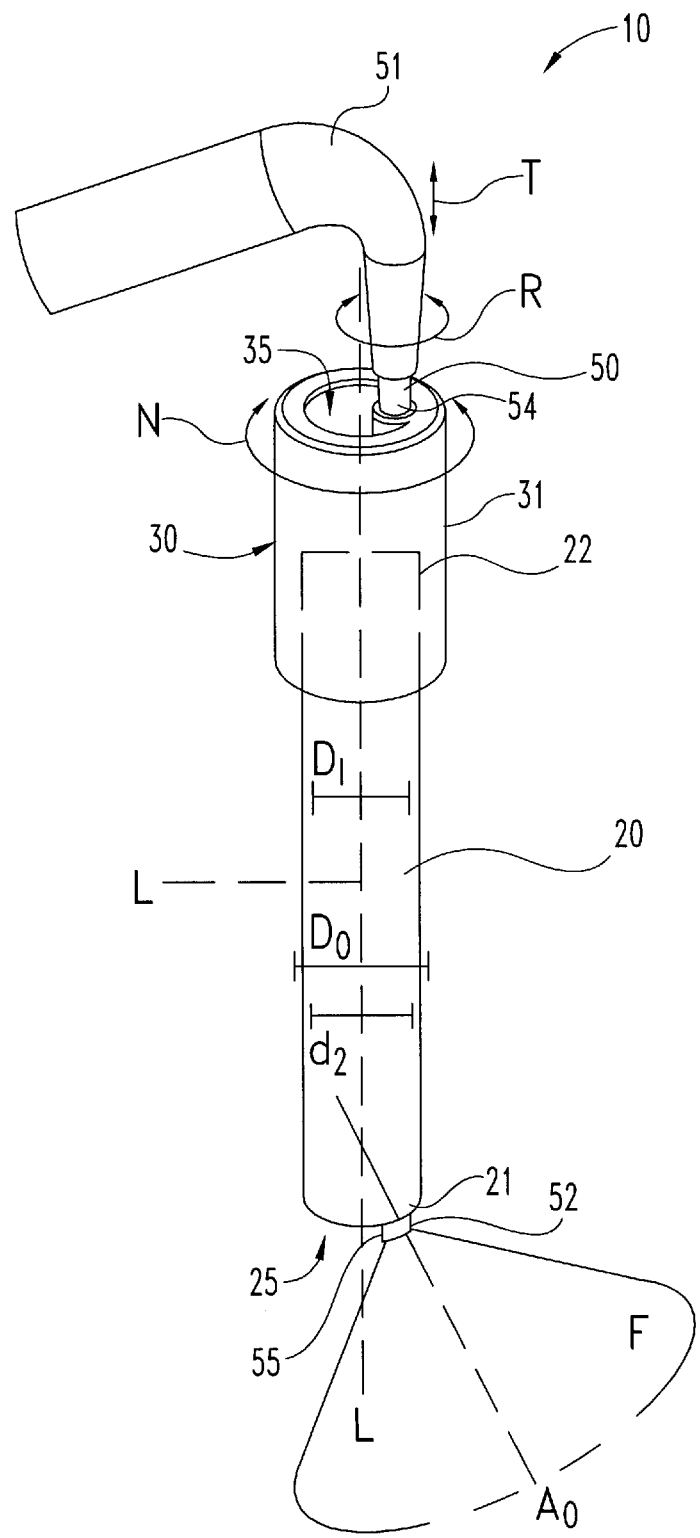
FIG. 1 is a side elevational view of a device according to this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and described methods, and such further applications of the principles of the invention as illustrated therein being contemplated as would normally occur to one skilled in the art to which the invention relates.

The present invention provides instruments and methods for performing percutaneous surgery, including spinal applications such as laminotomy, laminectomy, foramenotomy, facetectomy or discectomy, with a single working channel endoscope. The present inventors have discovered that many percutaneous surgeries may be performed without a fluid workspace through the use of optics which move independently of the cannula. The present invention contemplates techniques and instruments that can be implemented with or without a fluid environment.

This invention also brings the advantages of percutaneous procedures to applications that previously required open surgery. One advantage is based upon the further discovery that bone work can be performed percutaneously through a large working channel. Another advantage is realized in the use of a single portal within the patient to perform a wide range of simultaneous procedures.

According to one embodiment of the present invention, as depicted in FIG. 1, a device 10 is provided for use in percutaneous surgery which includes an elongated cannula 20 having a first inner diameter $D_I$ and an outer diameter $D_O$ sized for percutaneous introduction into a patient. The cannula 20 also includes a distal working end 21 and an opposite proximal end 22. The cannula defines a working channel 25 between the ends 21, 22 having a second diameter $d_2$ equal to the first inner diameter $D_I$ sized for receiving a tool therethrough. The cannula has a length along its longitudinal axis L that is sized to pass through the patient from the skin to an operative site or working space. In some cases, the working space may be adjacent a vertebra or disc, or in the spinal canal.

An elongated viewing element 50 is mountable inside cannula 20 adjacent the working channel 25. The viewing element 50 has a first end 51 connectable to a viewing apparatus, such as an eyepiece or camera, and an opposite second end 52 disposed or positionable adjacent the distal working end 21 of the cannula 20. The particular elongated viewing element 50 is not critical to the invention. Any suitable viewing element is contemplated that creates an optical or image transmission channel. In one embodiment, the elongated viewing element 50 includes a fiber optic scope 54 and a lens 55 at the second end 52. Preferably, the fiber optic scope includes illumination fibers and image transmission fibers (not shown). Alternatively, the viewing element may be a rigid endoscope or an endoscope having a steerable or bendable tip.

One advantage of this invention is that it provides optics which are movable relative to the cannula 20. Because the optics are movable, it is not necessary to provide a fluid-maintained work space. The optics can be removed, cleaned and replaced while the cannula is percutaneously positioned within the patient over the working space. Any configuration which allows the optics to be movably supported adjacent the working channel 25 is contemplated. In one embodiment, shown in FIGS. 1–3, a fixture 30 is provided for mounting the elongated viewing element 50 to the cannula 20. Preferably, the fixture 30 includes a housing 31 attachable to the proximal end 22 of the cannula 20. The working channel opening 35 is sized to substantially correspond to the second diameter $d_2$ of the working channel 25 to receive tools. The fixture 30 includes a housing 31 which defines a working channel opening 35 arranged to communicate with the working channel 25 when the fixture 30 is mounted to the cannula 20. The working channel opening 35 is sized to receive tools therethrough for passage through the working channel 25. In the embodiments shown in FIGS. 1–3, the fixture 30 is configured to mount the viewing element 50 within the working channel 25.

The housing 31 also defines an optics bore 60 adjacent the working channel opening 35. The optics bore 60 has a longitudinal axis $\ell$ that is preferably substantially parallel to the axis L of the cannula and working channel. The optics bore 60 is preferably sized to removably receive the elongated viewing element 50 therethrough. The fixture 30 preferably supports the viewing element 50 for movement within the optics bore 60 along the longitudinal axis of the bore 60 to extend or retract the lens 55 relative to the distal working end 21 of the cannula 20. The retractable/extendable feature of the optics of this invention provides an advantage over prior endoscopes because it eliminates the requirement for a fluid workspace. While the device 10 and its viewing element 50 can be easily used in a fluid environment, the fluid is not essential for the system to operate, contrary to prior systems. Furthermore, many of the prior endoscopes were not suited to access certain areas because of their large diameters. For example, prior endoscopes could not access the spinal canal. However, with this invention, access to the spinal canal is not limited by the diameter of the channel or cannula. The cannula 20 can be left behind in the soft tissue or supported by the lamina while the second end 52 of the elongated viewing element 50 can be advanced into the spinal canal along with any spinal instruments which have been inserted into the working channel 25.

Preferably the fixture 30 also supports the viewing element 50 for rotation within the optics bore 60 about the longitudinal axis $\ell$ of the bore 60. The lens 55 of the viewing element 50 defines an optical axis $A_O$. As in many endoscopes, the optical axis $A_O$ can be offset at an angle relative to the longitudinal axis $\ell$ of the optics bore 60. This feature allows the optical axis $A_O$ of the lens to be swept through a conical field of view F for greater visibility of the working space. The fixture 30 can further be configured so that the viewing element 50 is rotatable relative to the cannula 20. In this embodiment, the housing 31 is rotatable relative to the cannula 20 so that the second longitudinal axis $\ell$ of the optics bore 60 rotates about the longitudinal axis L of the working channel 25. The rotatable features of this invention allows visualization of the entire working space. This feature also aids in simplifying the surgical procedure because the optics 50 and accompanying fittings can be moved out of the way of the surgeon's hands and tools passing through the working channel.

Figure 3:
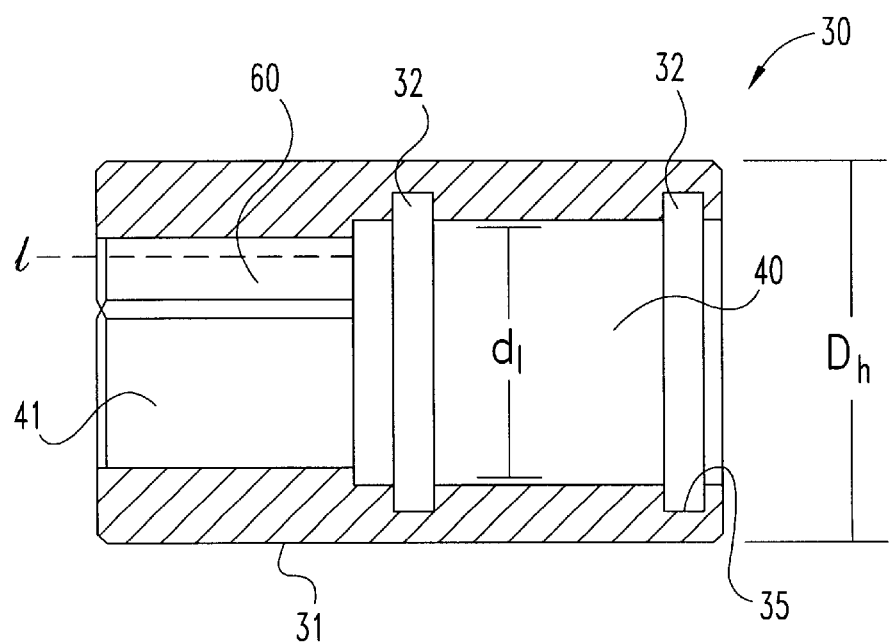
FIG. 3 is a side cross-sectional view of the fixture shown in FIG. 2.

In one embodiment depicted in FIG. 3, the housing 31 defines a receiver bore 40 having an inner diameter $d_I$ slightly larger than the outer diameter $D_O$ of the cannula 20. In this configuration, the proximal end 22 of the cannula 20 can be received within the receiver bore 40 so that the housing 31 can rotate about the proximal end 22 of the cannula 20. As shown in FIG. 3, the housing 31 also includes an upper bore 41 which is contiguous with the working channel opening 35 and the receiver bore 40. In one embodiment, the optics bore 60 is disposed within the upper bore 41 of the housing 31.

Figure 2:
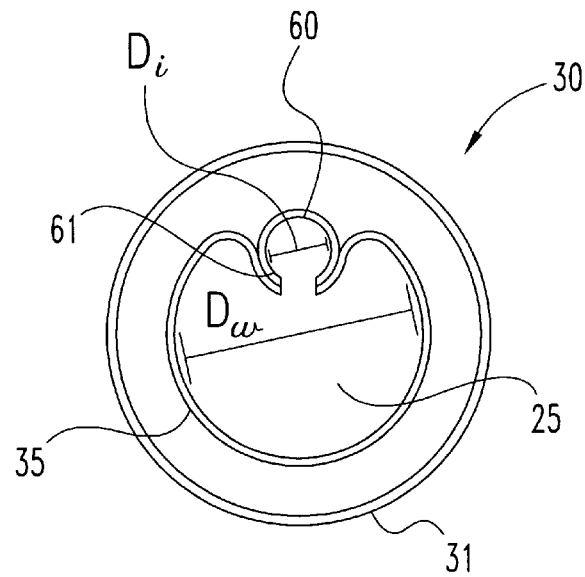
FIG. 2 is a top elevational view of a fixture for supporting a viewing device within a cannula according to this invention.

In a preferred embodiment depicted in FIG. 2, the optics bore 60 is defined by a C-shaped clip 61 disposed within the upper bore 41. Preferably, the C-shaped clip 61 is formed of a resilient material and the optics bore 60 defined by the clip 61 has an inner diameter $D_i$ that is slightly less than the outer diameter of the elongated viewing element 50. When the viewing element 50 is pushed into the optics bore 60 it resiliently deflects the C-shaped clip 61. The resilience of the clip 61 provides a gripping force on the element 50 to hold it in the desired position, while still allowing the element 50 to be repositioned.

Alternatively, the optics bore 60 can have an inner diameter larger than the outer diameter of the viewing element. In this instance, the viewing element 50 can be supported outside the device 20, either manually or by separate support fixture.

Preferably the device 10 provides engagement means for securely yet rotatably engaging the fixture 30 to the cannula 20. Most preferably, the fixture 30 is configured to engage a standard cannula 20. Engagement means can be disposed between the housing 31 and the cannula 20 when the fixture 30 is mounted to the proximal end 22 of the cannula 20 for providing gripping engagement between the housing 31 and the cannula 20. In one embodiment depicted in FIG. 3 the engagement means includes a number of grooves 32 within the receiver bore 40 and a resilient sealing member, such as an O-ring (see FIG. 11) disposed in each groove 32. The sealing members, or O-rings, disposed between the housing 31 and the outer diameter $D_O$ of the cannula 20 rotatably secure the fixture 30 to the cannula 20. The O-rings provide sufficient resistance to movement to hold the fixture 30 in a selectable position on the cannula. In another embodiment, the housing 31 defines a receiver bore 40 which has an inner diameter $d_I$ which is only slightly larger than the outer diameter $D_O$ of the cannula 20 so that the housing 31 can rotate freely about the cannula 20.

The working channel 25 and the working channel opening 35 are both sized to receive a tool or instrument therethrough. Preferably, the working channel opening 35 of the housing 31 has a diameter Dw which is substantially equal to the inner diameter $d_2$ of the working channel 25 so that the effective diameter of the working channel is not reduced by the fixture 30. This configuration provides a maximum amount of space for the insertion of tools into the working channel 25. The present invention is advantageous because standard micro-surgical spinal tools can be inserted into the working channel and manipulated to perform a surgical procedure. The present invention is particularly advantageous because the working channel 25 will simultaneously accept a plurality of movable instruments. No other known prior art device has a working channel that accepts more than one movable instrument at a time through a single port. Therefore, according to this invention, an entire percutaneous surgical procedure can be performed through the working channel 25 of the device 10 under direct visualization using the viewing element 50 disposed within the optics bore 60.

Although standard micro-surgical instruments may be used with the present invention, this invention also contemplates certain novel tools which capitalize on and enhance the advantages of this invention.

Figure 4:
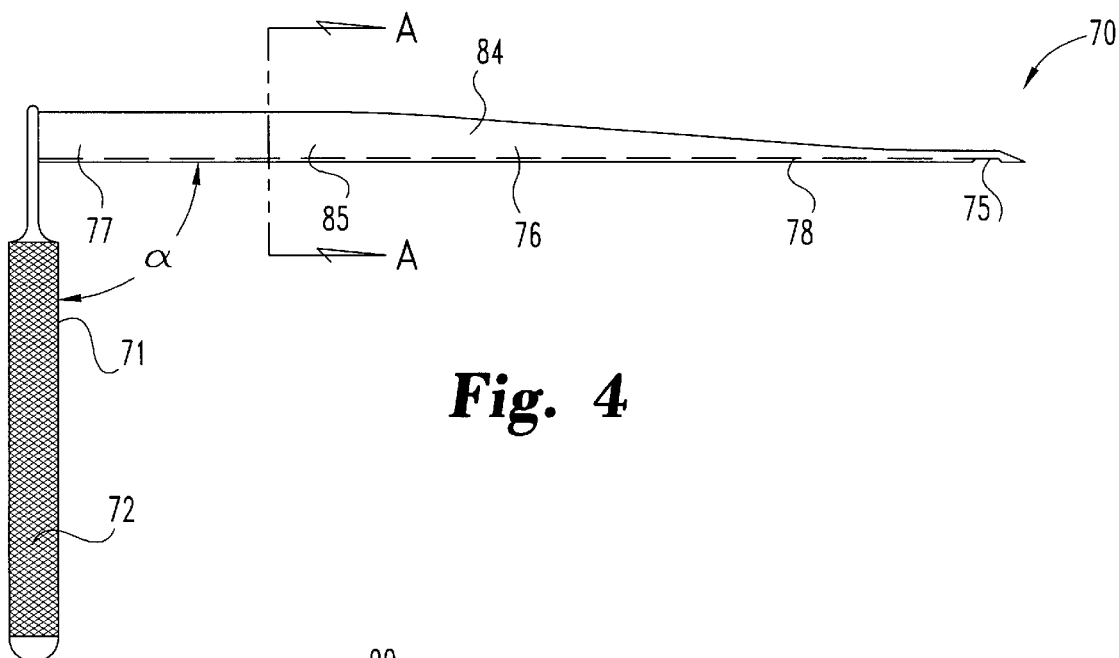
FIG. 4 is a side elevational view of a retractor according to one embodiment of this invention.
Figure 4A:
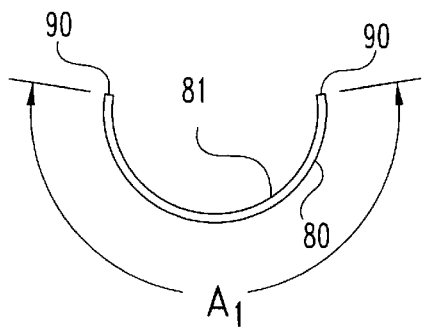
FIG. 4A is an end cross-sectional view of the retractor of FIG. 4 taken along lines A—A.
Figure 5:
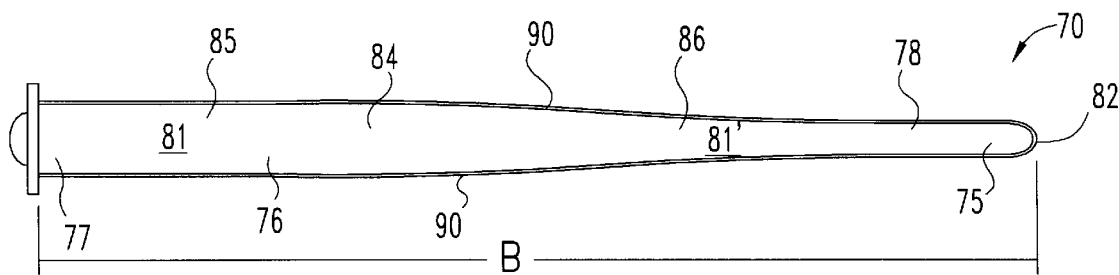
FIG. 5 is a top elevational view of the retractor shown in FIG. 4.
Figure 6:
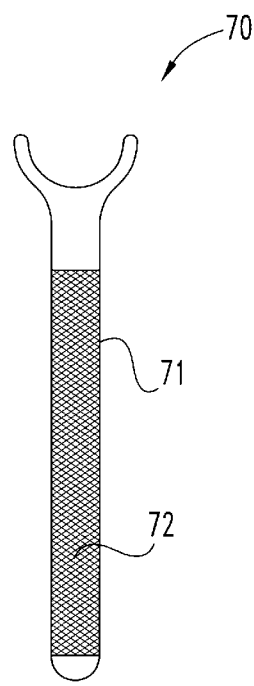
FIG. 6 is an end elevational view of the retractor shown in FIGS. 4 and 5.
Figure 7A:
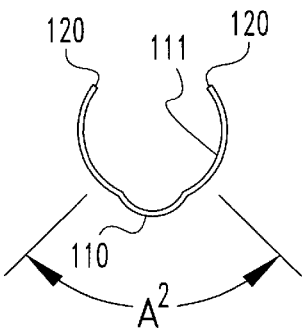
FIG. 7A is an end cross-sectional view of the retractor of FIG. 7 taken along lines A—A.
Figure 7B:
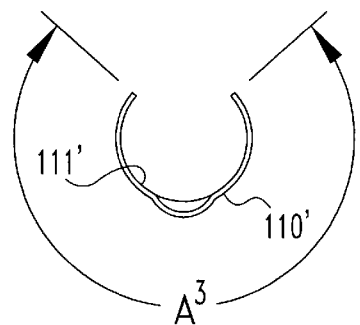
FIG. 7B is an end cross-sectional view of the retractor of FIG. 7 taken along lines B—B.
Figure 7:
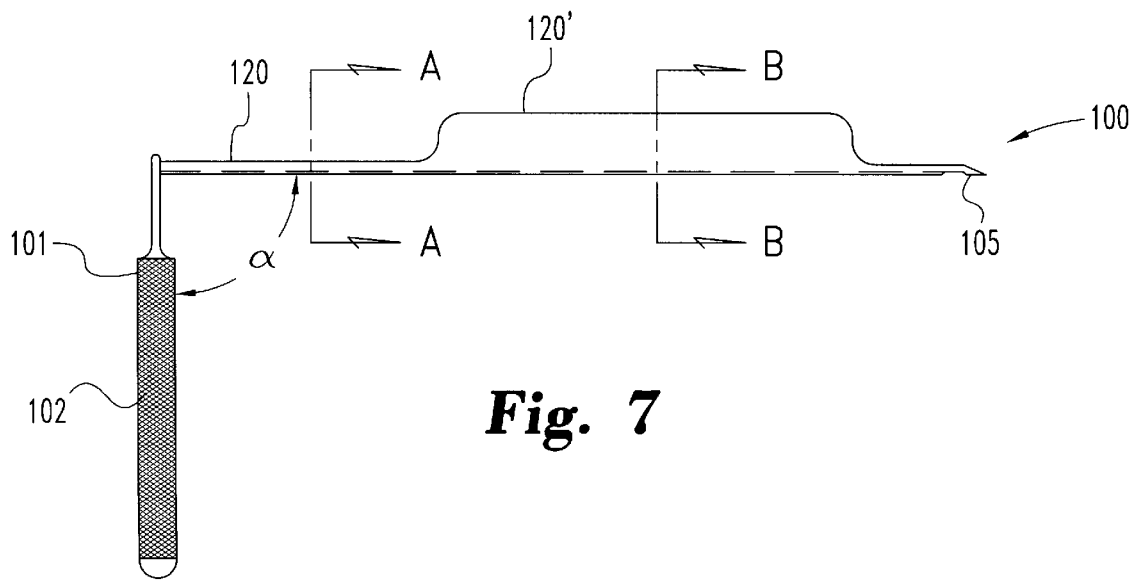
FIG. 7 is a side elevational view of a retractor according to another embodiment of this invention.

According to one preferred embodiment of the invention, a tissue retractor 70 is provided as depicted in FIGS. 4–6. The retractor 70 is removably and rotatably insertable through the working channel 25 and the working channel opening 35 of the device 10. The tissue retractor 70 includes a working tip 75 configured to atraumatically displace tissue as the retractor 70 is manipulated through the tissue and a body 76 having a proximal first end 77 and a distal second end 78. The second end 78 can be integral with the working tip 75 which preferably has a blunt curved end 82. In addition, the working tip 75 is also preferably bent or curved away from the body 76, as shown in FIG. 7. The body 76 is sized to be rotatably received within the cannula 20 and has a length B from the first end 77 to the second end 78 sufficient so that the first end 77 and the working tip 75 can both extend outside the cannula 20 when the body 76 is within the cannula 20.

This invention contemplates any suitable retractor for use through the working channel 25. However, retractors such as the retractor 70 depicted in FIGS. 4–6 are preferred in which the body 76 includes a curved plate 84 that is configured to conform to the inner cylindrical surface 26 of the cannula without substantially blocking the working channel 25. The curved plate 84 has a convex surface 80 and an opposite concave surface 81. In one embodiment, the curved plate 84 includes a first plate portion 85 defining a first convex surface 80 and an opposite first concave surface 81. A second plate portion 86 is integral with the first plate portion 85 and is disposed between the first plate portion 85 and the working tip 75. The second plate portion 86 defines a second convex surface (not shown) and an opposite second concave surface 81'. Both the first plate portion 85 and the second plate portion 86 include opposite edges 90 extending substantially parallel to the length B of the body 76.

Preferably, the curved plate 84 subtends an arc $A_1$ between the opposite edges 90 of at least 200 degrees, and most preferably 270 degrees. In a specific embodiment, the second plate portion 86 and specifically the second concave surface 81' subtends an angle that decreases along the length of the retractor. Thus, in an embodiment, the second concave surface 81' subtends an angle of about 200 degrees adjacent the first plate portion 85, decreasing to an angle of less than about 10 degrees at end 78.

Figure 8:
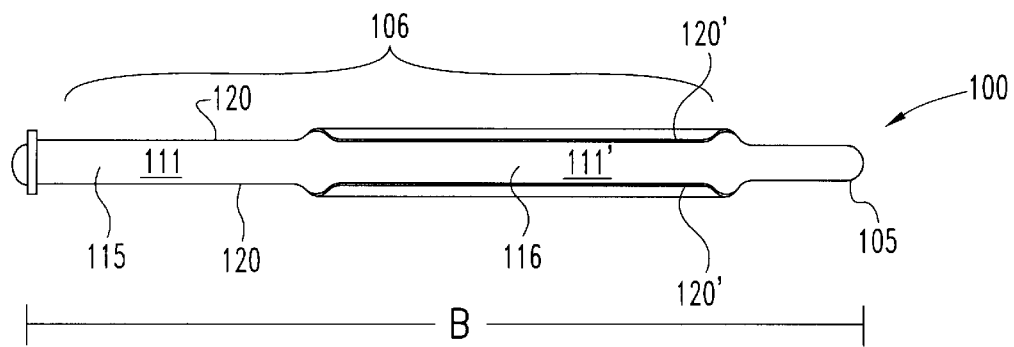
FIG. 8 is a top elevational view of the retractor shown in FIG. 7.

An alternate embodiment of a tissue retractor according to this invention is depicted in FIGS. 7–8. This retractor 100 has a body 106 which includes a first plate portion 115 defining a first convex surface 110 and an opposite first concave surface 111 and includes first opposite edges 120 extending substantially parallel to the length B of the body 106. The first plate portion 115 subtends a first arc $A_2$ between the first opposite edges 120. The retractor body 106 also includes a second plate portion 116 which is integral with the first plate portion 115 and is disposed between the first plate portion 115 and a working tip 105. The second plate portion 116 defines a second convex surface 110' and an opposite second concave surface 111' and includes second opposite edges 120' extending substantially parallel to the length B. The second plate portion 116 subtends a second arc $A_3$ between the second opposite edges 120' that is different from the first arc $A_2$ in this embodiment. Preferably, the first arc $A_2$ subtends an angle of less than 180 degrees and the second arc $A_3$ subtends an angle of more than 180 degrees. Most preferably, the first arc $A_2$ subtends an angle of about 90 degrees and the second arc $A_3$ subtends an angle of about 270 degrees.

The retractors of this invention may be provided with means for engaging the retractors 70, 100 within the working channel 25 of the cannula 20. For example, the convex surfaces 80, 110 can be configured to have a diameter that is greater than the diameter $D_I$ of the inner cylindrical surface 26 of the cannula 20. In that case, the body 76, 106 may be formed of a resilient material that is deformable to be insertable into the cannula 20 so that the convex surface 80, 110 is in contact with the inner cylindrical surface 26 of the cannula 20. When the body 76, 106 is deformed, it exerts an outward force against the surface 26 to frictionally hold the retractor in its selected position.

The preferred components provided by this invention are configured so that multiple tools and instruments can be accepted and manipulated within the working channel 25 of the cannula 20. The components are also configured so that more than one surgeon may manipulate instruments through the working channel 25 of the cannula 20 at one time. For example, one surgeon may be manipulating the retractor while another surgeon is drilling into a bone. The curvature of the body 76, 106 of the retractors 70, 100 provides more working space and increases visibility. Another feature is that the long axis of the component can be placed in the working channel 25 while a bend in the handle portion keeps hands away from the channel 25 so that more than one surgeon can work in the channel 25 and more tools can be placed in the channel 25. The retractors shown in FIGS. 4–8 each comprise an arm 71, 101 attached to the proximal first end 77, 107 of the body 76, 106. Preferably, as shown in FIGS. 4–8, the arm 71, 101 is at an angle $\alpha$ which is less than 180 degrees from the longitudinal axis of the length L of the body 76. Most preferably, the angle $\alpha$ is about 90 degrees so that the arm 71, 101 is substantially perpendicular to the length L of the body 76, 106. Preferably, the arm 71, 101 has a gripping surface 72, 102 to facilitate manipulation of the retractor 70, 100.

Figure 9:
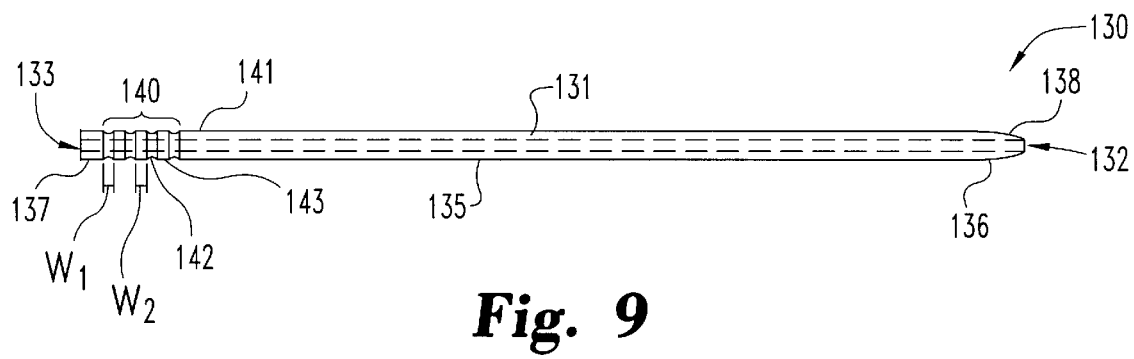
FIG. 9 is a side elevational view of a dilator according to this invention.

The present invention also provides tissue dilators usable with the device 10. Any dilator which is insertable into the working channel 25 of the cannula 20 is contemplated; however, a preferred dilator provided by this invention is depicted in FIG. 9. A dilator 130 preferably includes a hollow sleeve 135 defining a channel 131. The channel 131 allows the dilator 130 to be placed over a guidewire (not shown) or other dilators. The hollow sleeve 135 has a working end 136 defining a first opening 132 in communication with the channel 131 and an opposite end 137 defining a second opening 133. The working end 136 is tapered to a tapered tip 138 to atraumatically displace tissue. Preferably, a gripping portion 140 is provided on the outer surface 141 of the sleeve 135 adjacent the opposite end 137. In one embodiment, the gripping portion 140 is defined by a plurality of circumferential grooves 142 defined in the outer surface 141. The grooves 142 are configured for manual gripping of the dilator 130 to manipulate the dilator 130 through tissue. Preferably, the grooves 142 are partially cylindrical. In the embodiment shown in FIG. 9, the gripping portion 140 includes a number of circumferential flats 143 each of the circumferential grooves 142. The grooves 142 have a first width $W_1$ along the length of the sleeve 135 and the flats 143 have a second width $W_2$ 146 along the length.

Preferably, the first and second widths $W_1$ and $W_2$ are substantially equal.

The present invention has application to a wide range of surgical procedures, and particularly spinal procedures such as laminotomy, laminectomy, foramenotomy, facetectomy and discectomy. Prior surgical techniques for each of these procedures has evolved from a grossly invasive open surgeries to the minimally invasive techniques represented by the patents of Kambin and Shapiro. However, in each of these minimally invasive techniques, multiple entries into the patient is required. Moreover, most of the prior minimally invasive techniques are readily adapted only for a posterolateral approach to the spine. The devices and instruments of the present invention have application in an inventive surgical technique that permits each of these several types of surgical procedures to be performed via a single working channel. This invention can also be used from any approach and in other regions besides the spine.

The steps of a spinal surgical procedure in accordance with one aspect of the present invention are depicted in FIG. 10. As can be readily seen from each of the depicted steps (a)–(i), the present embodiment of the invention permits a substantially mid-line or medial posterior approach to the spine. Of course, it is understood that many of the following surgical steps can be performed from other approaches to the spine, such as posterolateral and anterior. In a first step of the technique, a guidewire 150 can be advanced through the skin and tissue into the laminae M of a vertebral body V. Preferably, a small incision is made in the skin to facilitate penetration of the guidewire through the skin. In addition, most preferably the guidewire, which may be a K-wire, is inserted under radiographic or image guided control to verify its proper positioning within the laminae L of the vertebra V. It is, of course, understood that the guidewire 150 can be positioned at virtually any location in the spine and in any portion of a vertebra V. The positioning of the guidewire is dependent upon the surgical procedure to be conducted through the working channel cannula of the present invention. Preferably, the guidewire 150 is solidly anchored into the vertebral bone, being tapped by a mallet if necessary.

In subsequent steps of the preferred method, a series of tissue dilators are advanced over the guidewire 150, as depicted in steps (b)–(d) in FIG. 10. Alternatively, the dilators can be advanced through the incision without the aid of a guidewire, followed by blunt dissection of the underlying tissues. In the specific illustrated embodiment, a series of successively larger dilators 151, 152 and 153 are concentrically disposed over each other and over the guidewire 150 and advanced into the body to sequentially dilate the perspicuous soft tissues. Most preferably, the tissue dilators are of the type shown in FIG. 9 of the present application. In a specific embodiment, the dilators have successively larger diameters, ranging from 5 mm, to 9 mm to 12.5 mm for the largest dilator. Other dilator sizes are contemplated depending upon the anatomical approach and upon the desired size of the working channel.

In the next step of the illustrated technique, the working channel cannula 20 is advanced over the largest dilator 153, as shown in step (e), and the dilators and guidewire 150 are removed, as shown in step (f). Preferably, the working channel cannula 20 has an inner diameter $D_I$ of 12.7 mm so that it can be easily advanced over the 12.5 mm outer diameter of the large dilator 153. Larger working channel cannulas are contemplated depending upon the anatomical region and surgical procedure.

With the cannula 20 in position, a working channel is formed between the skin of the patient to a working space adjacent the spine. It is understood that the length of the cannula 20 is determined by the particular surgical operation being performed and the anatomy surrounding the working space. For instance, in the lumbar spine the distance between the laminae M of a vertebra V to the skin of the patient requires a longer cannula 20 than a similar procedure performed in the cervical spine where the vertebral body is closer to the skin. In one specific embodiment in which the cannula 20 is used in a lumbar discectomy procedure, the cannula has a length of 87 mm, although generally only about half of the length of the cannula will be situated within the patient during the procedure.

In accordance with the present surgical technique, the working channel cannula 20 is at least initially only supported by the soft tissue and skin of the patient. Thus, in one aspect of the preferred embodiment, the cannula 20 can include a mounting bracket 27 affixed to the outer surface of the cannula (FIG. 10(f), FIG. 11). This mounting bracket 27 can be fastened to a flexible support arm 160, which can be of known design. Preferably, the flexible support arm 160 is engaged to the bracket 27 by way of a bolt and wing nut 161, as shown in FIG. 10 (i) and in more detail in FIG. 11, although other fasteners are also contemplated. This flexible arm 160 can be mounted on the surgical table and can be readily adjusted into a fixed position to provide firm support for the cannula 20. The flexible arm 160 is preferred so that it can be contoured as required to stay clear of the surgical site and to allow the surgeons adequate room to manipulate the variety of tools that would be used throughout the procedure.

Returning to FIG. 10, once the cannula 20 is seated within the patient, the fixture 30 can be engaged over the proximal end of the cannula 20. The fixture 30, as shown in FIGS. 2 and 3 and as described above, provides an optics bore 60 for supporting an elongated viewing element, such as element 50 shown in step h. In accordance with the invention, the viewing element 50 is advanced into the fixture 30 and supported by the optics bore 60 (FIG. 2). In one specific embodiment, the element 50 is most preferably a fiber optic scope, although a rod lens scope or other viewing scopes may be utilized. In the final step (i) of the procedure shown in FIG. 10, the flexible arm 160 is mounted to the bracket 27 to support the cannula 20 which in turn supports the optical viewing element 50. This final position of step (i) in FIG. 10 is shown in more detail in FIG. 11. The viewing element 50 can be of a variety of types, including a rigid endoscope or a flexible and steerable scope.

Figure 11:
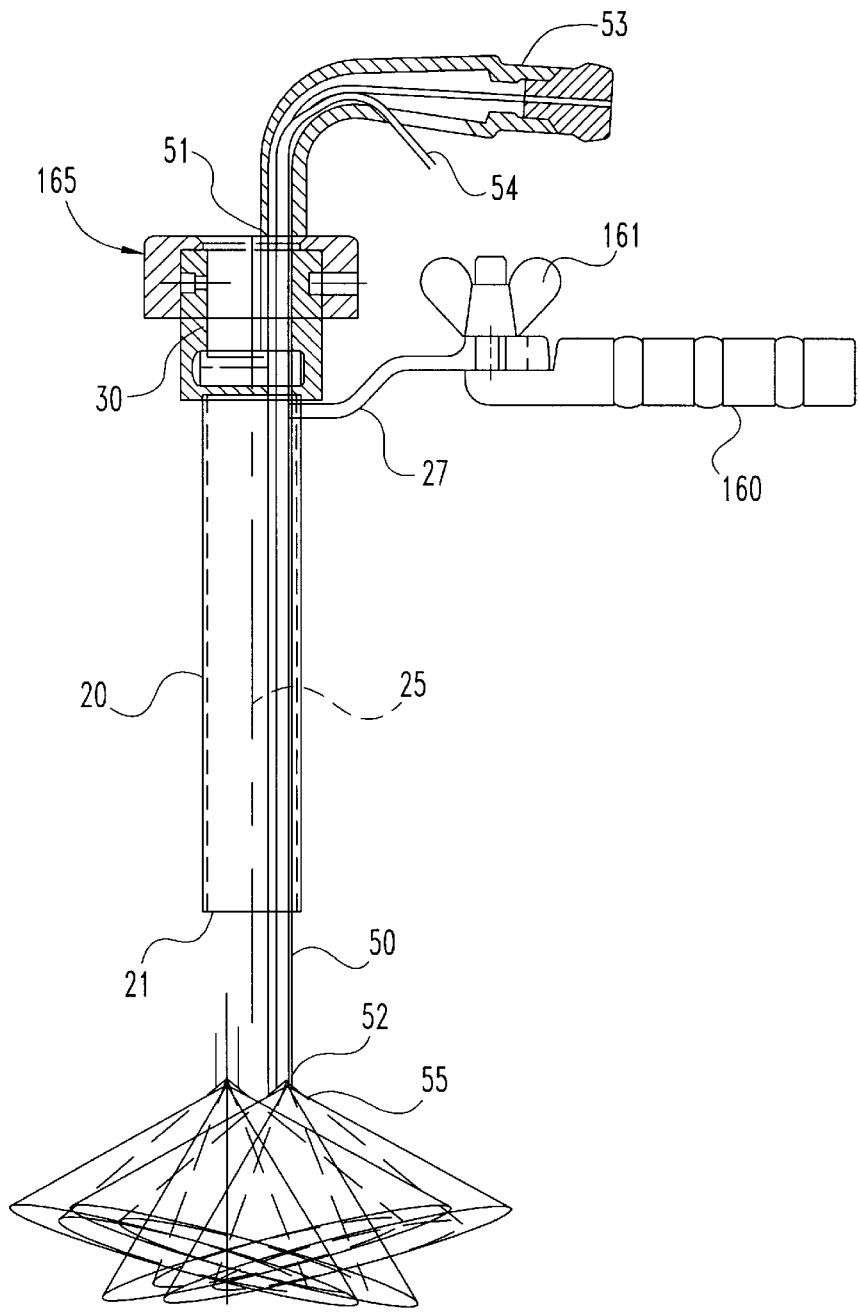
FIG. 11 is a side cross-sectional view of a device according to one embodiment of this invention.

With the viewing element or scope 50 supported by the fixture 30 the surgeon can directly visualize the area beneath the working channel 25 of the cannula 20. The surgeon can freely manipulate the viewing element 50 within the working channel 25 or beyond the distal end of the cannula into the working space. In the case of a steerable tip scope, the second end 52 of the viewing element 50, which carries the lens 55, can be manipulated to different positions, such as shown in FIG. 11. With virtually any type of viewing element, the manipulation and positioning of the scope is not limited by the working channel 25, in contrast to prior systems.

Preferably, the positioning capability provided by the fixture 30 is utilized to allow extension of the lens 55 into the working space or retraction back within the cannula 20, as depicted by the arrows T in FIG. 1. Also the fixture preferably accommodates rotation of the element 50 about its own axis (arrows R in FIG. 1) to vary the viewing angle provided by the angled lens 55, or rotation of the entire viewing element 50 about the cannula 20 and around the circumference of the working channel 25, as shown by the arrows N in FIG. 1. In this manner, the surgeon is provided with a complete and unrestricted view of the entire working space beneath the working channel 25. In instances when the fixture 30 is rotated about the cannula 20, the viewing orientation of the optics (i.e., left-right and up-down) is not altered so the surgeon's view of the procedure and surrounding anatomy is not disturbed.

Another advantage provided by the single working channel cannula 20 of the present invention, is that the cannula can be readily positioned over an appropriate target tissue or bone, to thereby move the working space as necessary for the surgical procedure. In other words, since the working channel cannula 20 is freely situated within the patient's skin and tissue, it can be manipulated so that the working space beneath the cannula 20 is more appropriately centered over the target region of the spine. Repositioning of the cannula 20 can be performed under fluoroscopic guidance. Alternatively, the cannula may be fitted with position sensing devices, such as LEDs, to be guided stereotactically. As the cannula is being repositioned, the surgeon can also directly visualize the spine through the viewing element 50.

Once the position of the cannula 20 is established and a working space is oriented over the proper target tissue, a variety of tools and instruments can be extended through the working channel 25 to accomplish the particular surgical procedure to be performed. For instance, in the case of a laminotomy, laminectomy, foramenotomy or facetectomy, a variety of rongeurs, curettes, and trephines can be extended through the working channel opening 35 (see FIG. 2) and through the working channel 25 of the cannula 20 (see FIG. 11) into the working space. It is understood that these various tools and instruments are designed to fit through the working channel. For instance, in one specific embodiment, the working channel 25 through the cannula 20 can have a maximum diameter $d_2$ of 12.7 mm. However, with the viewing element 50 extending into the working channel 25, the effective diameter is about 8 mm in the specific illustrated embodiment, although adequate space is provided within the working channel 25 around the viewing element 50 to allow a wide range of movement of the tool or instrument within the working channel. The present invention is not limited to particular sizes for the working channel and effective diameter, since the dimensions of the components will depend upon the anatomy of the surgical site and the type of procedure being performed.

Preferably, each of the tools and instruments used with the working channel cannula 20 are designed to minimize obstruction of the surgeon's visualization of and access to the working space at the distal end of the working channel cannula. Likewise, the instruments and tools are designed so that their actuating ends which are manipulated by the surgeon are displaced from the working channel cannula 20. One such example is the tissue retractor shown in FIGS. 4–8. With these retractors, the handles that are manually gripped by the surgeon are offset at about a 90 degree angle relative to the longitudinal axis of the tool itself.

In accordance with once aspect of the present invention, the surgical procedures conducted through the working channel cannula 20 and within the working space at the distal end of the cannula are performed "dry"—that is, without the use of irrigation fluid. In prior surgical techniques, the working space at the surgical site is fluid filled to maintain the working space and to assist in the use of the visualization optics. However, in these prior systems the visualization optics were fixed within the endoscope. In contrast, the device 10 of the present invention allows a wide range of movement for the viewing element 50 so that the lens 55 can be retracted completely within the working channel 25 of the cannula 20 to protect it from contact with the perspicuous tissue or blood that may be generated at the surgical site.

Moreover, since the viewing element 50 is removable and replaceable, the element 50 can be completely removed from the fixture 30 so that the lens 55 can be cleaned, after which the viewing element 50 can be reinserted into the fixture and advanced back to the working space. Under these circumstances, then, the need for irrigation is less critical. This feature can be of particular value when cutting operations are being performed by a power drill. It has been found in prior surgical procedures that the use of a power drill in a fluid environment can cause turbulence or cavitation of the fluid. This turbulence can completely shroud the surgeon's view of the surgical site at least while the drill is being operated. With the present invention, the dry environment allows continuous viewing of the operation of the power drill so that the surgeon can quickly and efficiently perform the necessary cutting procedures.

While the present invention permits the surgeon to conduct surgical procedures in the working space under a dry environment, irrigation may be provided separately through the working channel 25. Alternatively, the viewing device 50 itself may include a tube 54 supported by the fitting 53 through which modest amounts of fluid can be provided to keep the visualization space clear. In addition, during a discectomy, aspiration of the excised tissue is preferred, and irrigation will frequently assist in rapid removal of this tissue. Thus, separate irrigation and aspiration elements can also be inserted through the working channel 25 as required by the procedure.

Figure 12:
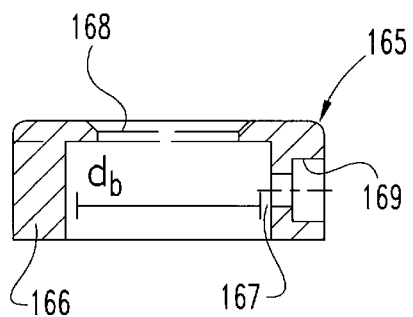
FIG. 12 is a side cross-sectional view of an aspiration cap as shown in FIG. 11.

As necessary, aspiration can be conducted directly through the working channel 25 of the cannula 20. In one specific embodiment, an aspiration cap 165 is provided as shown in FIGS. 11 and 12. The cap 165 includes a body 166 which defines a mating bore 167 having an inner diameter $d_b$ larger than the outer diameter $D_h$ of the housing 31 of fitting 30. A tool opening 168 is provided in communication with the mating bore 167. When the aspiration cap 165 is mounted over the housing 31, as shown in FIG. 11, the tool opening 168 communicates directly with the upper bore 41 and provides the same entry capabilities as the working channel opening 35 of the housing 31. The aspiration cap 165 is also provided with a tube receiver bore 169 which intersects the mating bore 167. The receiver bore 169 is configured to receive an aspiration tube through which a vacuum or suction is applied. In certain instances, the tool opening 168 may be covered while suction is applied through the tool receiver bore 169 and mating bore 167, and ultimately through the working channel 25. Covering the opening 168 can optimize the aspiration effect through the working channel.

Returning again to the surgical technique of one embodiment of the present invention, once the working channel cannula 20 and the optics 50 are in position, as depicted in FIG. 10 step (i) and FIG. 11, the paraspinous tissue can be reflected using instruments as described above, and a laminectomy performed using various rongeurs, curettes and drills. As necessary, the cannula 20 can be angled to allow a greater region of bone removal, which may be necessary for access to other portions of the spinal anatomy. In some instances, access to the spinal canal and the posterior medial aspects of the disc annulus may require cutting a portion of the vertebral bone that is greater than the inner diameter of the working channel 25. Thus, some manipulation of the cannula 20 may be necessary to permit removal of a greater portion of bone. In other operations, multi-level laminectomies or foramenotomies may be necessary. In this instance, these multi-level procedures can be conducted by sequentially inserting the working channel cannula 20 through several small cutaneous incisions along the spinal mid-line. Alternatively, several working channel cannulas 20 can be placed at each of the small cutaneous incisions to perform the multi-level bone removal procedures.

Again, in accordance with the preferred illustrated surgical technique, an opening is cut into the laminae M of the vertebra V providing direct visual access to the spinal canal itself. As necessary, tissue surrounding the spinal nerve root can be removed utilizing micro surgical knives and curettes. Once the spinal nerve root is exposed, a retractor, such as the retractors shown in FIGS. 4–8, can be used to gently move and hold the nerve root outside the working space. In one important aspect of the two retractors 70, 100, the portion of the retractor passing through the working channel 25 generally conforms to the inner surface of the cannula 20 so that the working channel 25 is not disrupted by the retractor tool. Specifically, the effective diameter within the working channel 25 is reduced only by the thickness of the curved plates 84, 114 of the retractors 70, 100. In one specific embodiment, this thickness is about 0.3 mm, so it can be seen that the tissue retractors do not significantly reduce the space available in the working channel 25 for insertion of other tools and instruments.

With the tissue retractor in place within the working channel 25, bone within the spinal canal, such as may occur in a burst fracture, can be removed with a curette or a high speed drill. Alternatively, the fractured bone may be impacted back into the vertebral body with a bone impactor. At this point, if the spinal procedure to be performed is the removal of epidural spinal tumors, the tumors can be resected utilizing various micro-surgical instruments. In other procedures, the dura may be opened and the intradural pathology may be approached with micro-surgical instruments passing through the working channel cannula 20. In accordance with the specific illustrated technique, with the nerve root retracted posterior medial disc herniations can be readily excised directly at the site of the herniation.

One important feature of the present invention is achieved by the large diameter of the working channel 25 in the cannula 20. This large diameter allows the surgeon or surgeons conducting the surgical procedure to introduce a plurality of instruments or tools into the working space. For example, as described above, a tissue retractor and discectomy instruments can be simultaneously extended through the working channel. In that illustrated embodiment, the discectomy instruments could include a trephine for boring a hole through the disc annulus and a powered tissue cutter for excising the herniated disc nucleus. Likewise, the present invention contemplates the simultaneous introduction of other types of instruments or tools as may be dictated by the particular surgical procedure to be performed. For example, an appropriately sized curette and a rongeur may be simultaneously extended through the working channel into the working space. Since all operations being conducted in the working space are under direct visualization through the viewing element 50, the surgeon can readily manipulate each of the instruments to perform tissue removal and bone cutting operations, without having to remove one tool and insert the other. In addition, since the surgical procedures can be conducted without the necessity of irrigation fluid, the surgeon has a clear view through the working space of the target tissue. Furthermore, aspects of the invention which permit a wide range of motion to the viewing element 50 allow the surgeon to clearly visualize the target tissue and clearly observe the surgical procedures being conducted in the working space.

The surgeon can capitalize on the same advantages in conducting a wide range of procedures at a wide range of locations in the human body. For example, facetectomies could be conducted through the working channel by simply orienting the working channel cannula 20 over the particular facet joints. The insertion of vertebral fixation elements can also be accomplished through the device 10. In this type of procedure, an incision can be made in the skin posterior to the location of the vertebra at which the fixation element is to be implanted. Implementing the steps shown in FIG. 10, the cannula 20 can be positioned through the incision and tissue directly above the particular location on the vertebra to be instrumented. With the optics extending through the working channel, an insertion tool holding the vertebral fixation element can be projected through the cannula 20 and manipulated at the vertebra. In one specific embodiment, the fixation element can be a bone screw. The working channel 25 has a diameter that is large enough to accept most bone screws and their associated insertion tools. In many instances, the location of the bone screw within the vertebra is critical, so identification of the position of the cannula 20 over the bony site is necessary. As mentioned above, this position can be verified fluoroscopically or using stereotactic technology.

In many prior procedures, cannulated bone screws are driven into the vertebra along K-wires. The present invention eliminates the need for the K-wire and for a cannulated screw. The working channel itself can effectively operate as a positioning guide, once the cannula 20 is properly oriented with respect to the vertebra. Moreover, the device 10 allows insertion of the bone screw into the vertebra to be conducted under direct vision. The surgeon can then readily verify that the screw is passing into the vertebra properly. This can be particularly important for bone screws being threaded into the pedicle of a vertebra. The working channel cannula 20 can be used to directly insert a self-tapping bone screw into the pedicle, or can accept a variety of tools to prepare a threaded bore within the pedicle to receive a bone screw.

The device 10 can also be used to prepare a site for fusion of two adjacent vertebrae, and for implantation of a fusion device or material. For example, in one surgical technique, an incision can be made in the skin posterior to a particular disc space to be fused. The incision can be made anteriorly, posteriorly or posterior laterally. If the incision is made anteriorly for anterior insertion of the working channel, it is anticipated that care will be taken to retract tissues, muscle and organs that may follow the path of the incision to the disc space. However, the device 10 of the present invention allows this tissue retraction to occur under direct vision so that the surgeon can easily and accurately guide the cannula 20 to the disc space without fear of injury to the surrounding tissue. As the tissue beneath the skin is successively excised or retracted, the working channel cannula 20 can be progressively advanced toward the anticipated working space adjacent the vertebral disc. Again under direct vision, the disc space can be prepared for implantation of fusion materials or a fusion device. Typically, this preparation includes preparing an opening in the disc annulus, and excising all or part of the disc nucleus through this opening.

In subsequent steps, a bore is cut through the disc annulus and into the endplates of the adjacent vertebrae. A fusion device, such as a bone dowel, a push-in implant or a threaded implant can then be advanced through the working channel of device 10 and into the prepared bore at the subject disc space. In some instances, the preparatory steps involve preparing the vertebral endplates by reducing the endplates to bleeding bone. In this instance, some aspiration and irrigation may be beneficial. All of these procedures can be conducted by tools and instruments extending through the working channel cannula 20 and under direct vision from the viewing element 50.

In some instances, graft material is simply placed within the prepared bore. This graft material can also be passed through the working channel cannula 20 into the disc space location. In other procedures, graft material or bone chips are positioned across posterior aspects of the spine. Again, this procedure can be conducted through the working channel cannula particularly given the capability of the cannula to be moved to different angles from a single incision site in the skin.

The present invention provides instruments and techniques for conducting a variety of surgical procedures. In the illustrated embodiments, these procedures are conducted on the spine. However, the same devices and techniques can be used at other places in the body. For example, an appropriately sized working channel device 10 can be used to remove lesions in the brain. The present invention has particular value for percutaneous procedures where minimal invasion into the patient is desirable and where accurate manipulation of tools and instruments at the surgical site is required. While the preferred embodiments illustrated above concern spinal procedures, the present invention and techniques can be used throughout the body, such as in the cranial cavity, the pituitary regions, the gastrointestinal tract, etc. The ability to reposition the viewing optics as required to visualize the surgical site allows for much greater accuracy and control of the surgical procedure. The present invention allows the use of but a single entry into the patient which greatly reduces the risk associated with open surgery or multiple invasions through the patient's skin.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A tissue retractor for use in percutaneous surgery through a cannula having an inner cylindrical surface, said retractor comprising:

a working tip configured to atraumatically displace tissue as the retractor is manipulated through the tissue; and a body having a proximal first end and a distal second end, said second end being integral with said working tip, said body sized to be rotatably received within the cannula and having a length from said first end to said second end sufficient so that said first end and said working tip can be outside the cannula when said body is within the cannula, said body having a convex surface extending along at least a portion of said length configured to conform to the inner surface of the cannula when said body and said working tip are disposed within the cannula, wherein said body includes:

a first plate portion defining a first convex surface and an opposite first concave surface and including first opposite edges extending substantially parallel to said length of said body, said first plate portion subtending a first arc between said first opposite edges; and a second plate portion integral with said first plate portion and disposed between said first plate portion and said working tip, said second plate portion defining a second convex surface and an opposite second concave surface and including second opposite edges extending substantially parallel to said length, said second plate portion subtending a second arc between said second opposite edges that is different from said first arc.

2. The tissue retractor of claim 1, wherein said first arc subtends an angle of less than 180 degrees and said second arc subtends an angle of more than 180 degrees.

3. The tissue retractor of claim of claim 1, wherein said first arc subtends an angle of about 90 degrees and said second arc subtends an angle of about 270 degrees.

4. The tissue retractor of claim 1, further comprising an arm attached to said proximal first end of said body, said arm having a gripping surface to facilitate manipulation of said tissue retractor.

5. The tissue retractor of claim 4, wherein said arm is substantially perpendicular to said length of said body.

6. A tissue retractor for use in percutaneous surgery through a cannula having an inner cylindrical surface, said retractor comprising:

a working tip configured to atraumatically displace tissue as the retractor is manipulated through the tissue;

a body having a proximal first end and a distal second end, said second end being integral with said working tip, said body having a convex surface configured to conform to the inner cylindrical surface of the cannula when said tissue retractor is disposed within the cannula, wherein said body is sized to be rotatably received within the cannula and has a length from said first end to said second end sufficient so that said first end and said working tip can be outside the cannula when said body is within the cannula, said body further including:

a first plate portion defining a first convex surface and an opposite first concave surface and including first opposite edges extending substantially parallel to said length of said body, said first plate portion subtending a first arc between said first opposite edges; and a second plate portion integral with said first plate portion and disposed between said first plate portion and said working tip, said second plate portion defining a second convex surface and an opposite second concave surface and including second opposite edges extending substantially parallel to said length, said second plate portion subtending a second arc between said second opposite edges that is different from said first arc, wherein said second arc subtends an angle that decreases along said length toward said working tip.

7. The tissue retractor of claim 6, wherein said second arc subtends an angle of about 200 degrees adjacent said first plate portion decreasing to an angle of less than 10 degrees adjacent said working tip.

8. The tissue retractor of claim 7, wherein said first arc subtends an angle of about 200 degrees.

9. A tissue retractor for use in percutaneous surgery through a cannula having an inner cylindrical surface, said retractor comprising:

a working tip configured to atraumatically displace tissue as the retractor is manipulated through the tissue; and a body having a proximal first end and a distal second end, said second end being integral with said working tip, said body having a convex surface configured to conform to the inner cylindrical surface of the cannula when said tissue retractor is disposed within the cannula, said body sized to be rotatably received within the cannula and having a length from said first end to said second end sufficient so that said first end and said working tip can be outside the cannula when said body is within the cannula, wherein said convex surface of said body is at a diameter that is greater than the diameter of the inner cylindrical surface of the cannula, said body being resiliently deformable to be insertable into the cannula with said convex surface in contact with the inner cylindrical surface of the cannula.

10. The tissue retractor of claim 9, wherein said working tip has a blunt curved end.

11. The tissue retractor of claim 9, wherein said body includes a curved plate defining said convex surface and an opposite concave surface.

12. The tissue retractor of claim 11, wherein said curved plate includes opposite edges extending substantially parallel to said length of said body, said curved plate subtending an arc between said opposite edges of at least 200 degrees.

13. The tissue retractor of claim 12, wherein said curved plate subtends an arc between said opposite edges of about 270 degrees.

14. The tissue retractor of claim 9, further comprising an arm attached to said proximal first end of said body, said arm having a gripping surface to facilitate manipulation of said tissue retractor.

15. The tissue retractor of claim 14, wherein said arm is substantially perpendicular to said length of said body.

16. A tissue retractor for use in percutaneous surgery through a cannula having an inner cylindrical surface, said retractor comprising:

a working tip configured to atraumaticaly displace tissue as the retractor is manipulated through the tissue; and a body having a proximal first end and a distal second end, said second end being integral with said working tip, said body having a convex surface defining a working channel between said first end and said second end configured to receive at least one surgical tool therethrough when said tissue retractor is disposed within the cannula, said body having a length from said first end to said second end sufficient so that said first end and said working tip can be outside the cannula when said body is within the cannula, wherein said body includes:

a first plate portion defining a first convex surface and an opposite first concave surface and including first opposite edges extending substantially parallel to said length of said body, said first plate portion defining a circular cross-section between said first opposite edges subtending a first arc; and a second plate portion integral with said first plate portion and disposed between said first plate portion and said working tip, said second plate portion defining a second convex surface and an opposite second concave surface and including second opposite edges extending substantially parallel to said length, said second plate portion defining a circular cross-section between said second opposite edges subtending a second arc that is different from said first arc.

17. The tissue retractor of claim 16, wherein said body is configured to conform to the inner surface of the cannula.

18. The tissue retractor of claim 17, wherein said body is rotatably received within the cannula.

19. The tissue retractor of claim 17, wherein said body includes a curved plate defining said convex surface and an opposite concave surface.

20. The tissue retractor of claim 19, wherein said curved plate includes opposite edges extending substantially parallel to said length of said body, said curved plate defining a circular cross-section extending between said opposite edges subtending an arc of at least 200 degrees.

21. The tissue retractor of claim 16, wherein said first arc subtends an angle of less than 180 degrees and said second arc subtends an angle of more than 180 degrees.

22. The tissue retractor of claim of claim 16, wherein said first arc subtends an angle of about 90 degrees and said second arc subtends an angle of about 270 degrees.

* * * * *